United States Patent [19]
Farinas et al.

[11] Patent Number: 5,906,830
[45] Date of Patent: May 25, 1999

[54] SUPERSATURATED TRANSDERMAL DRUG DELIVERY SYSTEMS, AND METHODS FOR MANUFACTURING THE SAME

[75] Inventors: Kathleen C. Farinas, Belmont, Calif.; Chad M. Miller, Durham, N.C.; Pravin L. Soni, Sunnyvale, Calif.

[73] Assignee: Cygnus, Inc., Redwood City, Calif.

[21] Appl. No.: 08/708,389

[22] Filed: Sep. 4, 1996

Related U.S. Application Data

[63] Continuation-in-part of application No. 08/525,867, Sep. 8, 1995, abandoned.

[51] Int. Cl.$^6$ ....................................................... A61F 13/02
[52] U.S. Cl. ............................................ 424/448; 424/449
[58] Field of Search .................................. 424/448, 449; 514/772.3

[56] References Cited

U.S. PATENT DOCUMENTS

| | | | |
|---|---|---|---|
| 4,409,206 | 10/1983 | Stricker | 424/444 |
| 4,746,509 | 5/1988 | Haggiage et al. | 424/449 |
| 4,832,953 | 5/1989 | Campbell et al. | 424/448 |
| 4,883,669 | 11/1989 | Chien et al. | 424/448 |
| 5,252,334 | 10/1993 | Chiang et al. | 424/448 |
| 5,332,576 | 7/1994 | Mantelle | 424/443 |
| 5,352,457 | 10/1994 | Jenkins | 424/448 |
| 5,364,629 | 11/1994 | Kochinke et al. | 424/449 |
| 5,474,783 | 12/1995 | Miranda et al. | 424/448 |

FOREIGN PATENT DOCUMENTS

| | | |
|---|---|---|
| 0 144 486 A2 | 6/1985 | European Pat. Off. . |
| 0 391 172 A1 | 10/1990 | European Pat. Off. . |
| 0 497 626 A1 | 8/1992 | European Pat. Off. . |
| 217 989 | 1/1985 | Germany . |
| 63093714 | 4/1988 | Japan . |
| WO 92 05811 | 4/1992 | WIPO . |
| WO94/10984 | 5/1994 | WIPO . |
| WO 97/09971 | 3/1997 | WIPO . |
| WO 97/24148 | 7/1997 | WIPO . |

OTHER PUBLICATIONS

Akhtar et al., "The Influence of Crystalline Morphology and Copolymer Composition on Drug Release From Solution Cast and Melt-processed P(HB-HV) Copolymer Matrices," *J. Controlled Release*(1991) 17 (3):225–234 cript.

Davis et al., "Effect of Supersaturation on Membrane Transport on Membrane Transport: 1. Hydrocortisone Actate," *Intl. J. of Pharm.* 76:1–8 (1991).

Pellet et al., "Effect of Supersaturation on Membrane Transport: 2. Piroxicam," *Intl. J. of Pharm.* 111:1–6 (1994).

*Primary Examiner*—Thurman K. Page
*Assistant Examiner*—Kathryne E. Shelborne
*Attorney, Agent, or Firm*—Barbara G. McClung; Bozicevic & Reed, LLP.

[57] ABSTRACT

Methods are provided for manufacturing transdermal drug delivery systems containing supersaturated drug reservoirs, such that higher drug fluxes are obtained. The methods involve heating the drug reservoir components to a predetermined temperature. Generally, this temperature is higher than the depressed melting temperature of the polymer-drug admixture which will serve as the drug reservoir. In an alternative embodiment, wherein heat treatment of the reservoir components results in a system having two liquid phases, the predetermined temperature is calculated so as to be higher than the melting temperature of the pure drug. Drug reservoirs and novel transdermal delivery systems prepared using the disclosed techniques are provided as well.

14 Claims, 6 Drawing Sheets

SUPERSATURATED TRANSDERMAL DRUG DELIVERY SYSTEMS, AND METHODS FOR MANUFACTURING THE SAME

CROSS-REFERENCE TO RELATED APPLICATION

This application is a continuation-in-part of U.S. patent application Ser. No. 08/525,867, filed Sep. 8, 1995, abandoned.

TECHNICAL FIELD

This invention relates generally to drug delivery, and more particularly relates to supersaturated transdermal drug delivery systems, i.e., transdermal devices containing a supersaturated drug reservoir, and to methods for manufacturing such systems.

BACKGROUND

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences—e.g., gastrointestinal irritation and the like—are eliminated as well. Transdermal drug delivery also makes possible a high degree of control over blood concentrations of any particular drug.

Skin is a structurally complex, relatively thick membrane. Molecules moving from the environment into and through intact skin must first penetrate the stratum corneum. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the cells of the stratum corneum which present the primary barrier to absorption of topical compositions or transdermally administered drugs. The stratum corneum is a thin layer of dense, highly keratinized cells approximately 10–15 microns thick over most of the body. It is believed to be the high degree of keratinization within these cells as well as their dense packing which creates in most cases a substantially impermeable barrier to drug penetration.

Relatively recent advances in transdermal drug delivery have enabled effective administration of a variety of drugs through the skin. These advances include the development of a number of skin penetration enhancing agents, or "permeation enhancers," to increase skin permeability, as well as non-chemical modes for facilitating transdermal delivery, e.g., the use of iontophoresis, electroporation or ultrasound. Nevertheless, the number of drugs that can be safely and effectively administered through the skin, without concomitant problems such as irritation or sensitization, remains limited.

The present invention is directed to novel drug delivery systems which have "supersaturated" drug reservoirs, and are thus able to deliver greater quantities of drug, at higher fluxes, than possible with prior transdermal systems. The novel delivery systems, by virtue of their supersaturated drug reservoirs, also reduce or in some cases eliminate the need for skin permeation enhancers. Further, smaller transdermal patches may be made using the inventive technology, i.e., patches that are at least as effective as prior patches in terms of overall drug release and drug flux, but are significantly reduced in terms of size.

None of the art of which applicants are aware describes transdermal drug delivery system having supersaturated drug reservoirs or methods for manufacturing such systems as disclosed and claimed herein. However, the following references are of interest:

U.S. Pat. No. 4,409,206 to Stricker relates to a method for preparing transdermal drug delivery systems containing the active substance in an amorphous form. Initially, a polyacrylate film is prepared by solvent casting. A drug solution or suspension is then applied to the film and the solvent is removed by evaporation. There is no disclosure concerning a heating step to dissolve the drug.

U.S. Pat. No. 4,746,509 to Haggiage et al. describes transdermal medicaments with the active ingredient dispersed in a drug reservoir in crystalline and/or solubilized form.

U.S. Pat. No. 4,832,953 to Campbell et al. describes a method for making drug delivery systems containing liquid drugs capable of forming crystalline hydrates. The drug delivery systems are heated above the melting temperature of the pure drug, after preparation of the systems, to prevent crystalline hydrate formation.

U.S. Pat. No. 4,883,669 to Chien et al. describes a transdermal drug delivery system for the administration of estradiol, wherein drug is microdispersed in a polymeric matrix disc layer which serves as the drug reservoir. The reservoir components are heated to a relatively low temperature, below the melting point of estradiol, during device manufacture.

U.S. Pat. No. 5,332,576 to Mantelle describes preparation of compositions for topical application, wherein drug is added to certain components, not including the bioadhesive carrier, and then heated at a temperature in the range of about 70° C. to 90° C. until all of the drug is dissolved. After the solution is cooled, the bioadhesive is added and the composition is applied to a backing material.

PCT Publication No. WO94/10984, inventors Horstmann et al., describes transdermal systems for the administration of estradiol, having drug concentrations in between the solubility of drug in the system when exposed to moisture and the solubility of the drug in the dry system. The system does not appear to be "supersaturated," if at all, until exposure to moisture. This is in contrast to the systems which may be prepared using the method of invention, which are supersaturated in the dry state. Hence, one would expect that systems from our invention would produce higher fluxes than those in this PCT publication.

Davis et al., "Effect of Supersaturation on Membrane Transport on Membrane Transport: 1. Hydrocortisone Acetate," *International Journal of Pharmaceutics* 76:1–8 (1991) and Pellet et al. "Effect of Supersaturation on Membrane Transport: 2. Piroxicam," *International Journal of Pharmaceutics* 111:1–6 (1994), present studies evaluating drug flux from supersaturated solutions of drug in propylene glycol/water formulations. Drug is first dissolved in solvent and then a supersaturated solution is made by added a second solvent thereto; no heating step is involved.

SUMMARY OF THE INVENTION

Accordingly, it is a primary object of the present invention to address the above-mentioned need in the art by providing methods for manufacturing transdermal drug delivery systems having supersaturated drug reservoirs, in turn enabling delivery of drug at an increased rate.

It is another object of the invention to provide a method for making such drug delivery systems, which method involves heating the components of the drug reservoir, during manufacture, to a carefully predetermined temperature, such that a supersaturated reservoir is produced.

It is another object of the invention to provide a transdermal system prepared using the aforementioned method, which comprises a laminated composite of a backing layer and a contact adhesive layer which is supersaturated with drug and serves as both the drug reservoir and the basal surface which contacts the skin or mucosal tissue during use.

It is still another object of the invention to provide a transdermal system prepared using the aforementioned method, which comprises a laminated composite of a backing layer, a contact adhesive layer which serves as the basal surface and contacts the skin or mucosal tissue during use, and, incorporated therebetween, a polymeric matrix which is supersaturated with drug and serves as the drug reservoir.

It is yet another object of the invention to provide a transdermal device prepared using the present method, comprising a laminated composite of a backing layer, a drug reservoir comprising a polymeric matrix supersaturated with drug, and a peripheral adhesive ring for affixing the device to the skin during use.

It is a further object of the invention to provide such methods and transdermal systems in which the drug to be delivered is one that is capable of phase separation into a low thermodynamic activity form such as a crystalline structure.

It is yet a further object of the invention to provide such methods and transdermal systems in which the drug to be delivered is one that exists as a solid at room temperature.

It is still a further object of the invention to provide such methods and transdermal systems in which the drug to be delivered is a steroid.

Additional objects, advantages and novel features of the invention will be set forth in part in the description which follows, and in part will become apparent to those skilled in the art upon examination of the following, or may be learned by practice of the invention.

In a primary aspect of the invention, a manufacturing method is provided for preparing supersaturated drug reservoirs to be incorporated into a transdermal drug delivery system. The method involves: (a) admixing a polymeric material and a drug formulation compatible therewith to form a drug-polymer admixture; (b) calculating the depressed melting temperature of the drug-polymer admixture; (c) heating the admixture prepared in step (a) to a predetermined temperature, effective to dissolve the drug in the polymeric material, wherein the predetermined temperature is above the depressed melting temperature calculated in step (b); and (d) cooling the heated admixture prepared in step (c) to form the drug reservoir, wherein the relative quantities of drug and polymeric material are such that the drug reservoir contains on the order of 0.1 wt. % to 20 wt. % drug.

In another aspect of the invention, an alternative manufacturing method is provided which involves: (a) admixing a polymeric material and a drug formulation compatible therewith to form a drug-polymer admixture; (b) heating the admixture prepared in step (a) to a predetermined temperature effective to provide a system containing two liquid phases, a first liquid phase comprising primarily polymeric material, and a second liquid phase comprising primarily drug formulation, wherein the predetermined temperature is such that it is higher than the actual melting temperature of the pure drug contained in the drug formulation; and (c) cooling the heated admixture prepared in step (b) to form the drug reservoir, wherein the relative quantities of drug and polymeric material are such that the drug reservoir contains on the order of 0.1 wt. % to 20 wt. % drug.

Methods for manufacturing transdermal systems are provided as well, comprising preparing a laminated composite of a supersaturated drug reservoir, a backing layer which serves as the upper surface of the device during use and is substantially impermeable to the drug, and a release liner to protect the basal surface of the device prior to use. Optionally, a contact adhesive layer or a peripheral ring of contact adhesive may be provided on the basal surface of the device to enable adhesion of the device to the skin during drug delivery.

Novel drug reservoirs and transdermal systems are provided using these unique manufacturing methods.

DETAILED DESCRIPTION OF THE INVENTION

Figure 1:
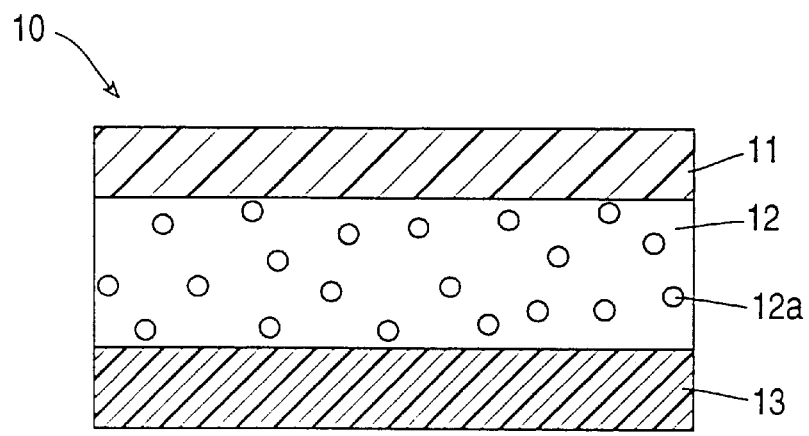
FIG. 1 illustrates in schematic form one embodiment of a solid matrix-type transdermal delivery system which may be manufactured so as to contain a supersaturated drug reservoir as provided herein.

Before describing the present invention in detail, it is to be understood that this invention is not limited to particular transdermal drug delivery device configurations, particular drug/vehicle formulations, or the like, as such may vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the content clearly dictates otherwise. Thus, for example, reference to "a permeation enhancer" includes a mixture of two or more permeation enhancers, reference to "an excipient" or "a vehicle" includes mixtures of excipients or vehicles, reference to "an adhesive layer" includes reference to two or more such layers, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

In describing and claiming the present invention, the following terminology will be used in accordance with the definitions set out below.

By "transdermal" delivery, applicants intend to include both transdermal (or "percutaneous") and transmucosal administration, i.e., delivery by passage of a drug through the skin or mucosal tissue and into the bloodstream.

By a "supersaturated" drug reservoir, as used herein, is intended a reservoir containing an amount of drug molecularly dispersed therein at a concentration greater than the solubility of the drug in the reservoir material at room temperature. The term "molecularly dispersed" in this context is intended to mean that the drug is "dissolved" in the reservoir material as opposed to a solid phase present therein; typically, then, the molecular dispersion of drug in reservoir material provided using the present technique is a single phase of drug and reservoir material.

By an "effective" amount of a drug is meant a nontoxic but sufficient amount of the drug to provide the desired therapeutic or prophylactic effect. An "effective" amount of a permeation enhancer as used herein means an amount that will provide the desired increase in skin permeability and, correspondingly, the desired depth of penetration, rate of administration, and amount of drug delivered.

By "predetermined area of skin" is intended a defined area of intact unbroken living skin or mucosal tissue. That area will usually be in the range of about 5 cm$^2$ to about 100 cm$^2$, more usually in the range of about 20 cm$^2$ to about 60 cm$^2$. However, it will be appreciated by those skilled in the art of transdermal drug delivery that the area of skin or mucosal tissue through which drug is administered may vary significantly, depending on patch configuration, dose, and the like. Also, as noted above, the present technology enables preparation of generally smaller patches, typically in the range of about 5 cm$^2$ to about 20 cm$^2$.

"Penetration enhancement" or "permeation enhancement" as used herein relates to an increase in the permeability of skin to a pharmacologically active agent, i.e., so as to increase the rate at which the drug permeates through the skin and enters the bloodstream. The enhanced permeation effected through the use of such enhancers can be observed by measuring the rate of diffusion of drug through animal or human skin using a diffusion cell apparatus as described in the Examples herein.

"Carriers" or "vehicles" as used herein refer to carrier materials suitable for transdermal drug administration, and include any such materials known in the art, e.g., any liquid, gel, solvent, liquid diluent, solubilizer, or the like, which is nontoxic and which does not interact with other components of the composition in a deleterious manner. Examples of suitable carriers for use herein include water, silicone, liquid sugars, waxes, petroleum jelly, and a variety of other materials. The term "carrier" or "vehicle" as used herein may also refer to stabilizers, crystallization inhibitors, or other types of additives useful for facilitating transdermal drug delivery.

The invention is based on the idea that heating the components of a drug reservoir to a carefully calculated, predetermined temperature can result in supersaturated systems which are able to deliver greater quantities of drug, at higher fluxes, than possible with prior transdermal systems. The methodology thus enables preparation of smaller patches, and can reduce or even eliminate the need for permeation enhancers.

The reservoir components include a polymeric material, preferably comprised of a pressure-sensitive adhesive material, and a drug formulation. Additional components may be present as well, as will be explained below. A phase diagram of the selected polymeric material and drug formulation is constructed using conventional techniques, i.e., Differential Scanning Calorimetry (DSC) or hot stage polarized optical microscopy, and the depressed melting temperature of the polymer-drug composition is calculated therefrom. Basically, a series of samples with a range of drug concentrations is evaluated by measuring the depressed melting temperature for each sample. The depressed melting temperature is the temperature at which all of the drug is dissolved in the polymer phase; in essence, this is equivalent to determining solubility as a function of temperature.

The depressed melting temperature of any particular polymer-drug admixture is thus the temperature at which the drug is completely dissolved in the polymer phase, forming a single phase solution. If more than one polymeric material is used, the temperature is such that the drug forms a single phase solution with each of the polymeric materials.

An admixture of polymer and drug is then heated to a temperature just higher than the calculated depressed melting temperature, but not so high as to result in chemical alteration or degradation of any reservoir component. Generally, the temperature will be less than about 40° C. greater than the depressed melting temperature, more typically less than about 10° C. greater than the depressed melting temperature, and most less than about 5° C. greater than the depressed melting temperature. Heating is continued until all of the drug is observed to dissolve in the selected polymeric material. As little as one or two minutes (or less) may be sufficient; however, with some systems, up to about several hours may be required. After heating, the mixture is cooled, yielding a supersaturated drug reservoir.

The aforementioned method, sometimes termed herein "Method A," is particularly useful with systems in which the selected drug has relatively high solubility in the polymeric material, typically greater than about 10 wt. %, preferably greater than about 20 wt. %, at the drug's melting temperature. This will be true with a number of polymeric materials, particularly acrylic adhesives and polyurethanes. However, each individual drug-polymer formulation will need to be evaluated independently, on this basis.

In an alternative embodiment, where heating a particular polymer-drug admixture results in a system with two liquid phases, the preferred temperature at which the admixture is heated to provide a supersaturated drug reservoir is calculated differently. In this case, one liquid phase will be present that primarily contains polymer, while a second liquid phase will be present that primarily contains drug. The latter phase, when quenched rapidly, becomes an amorphous, glassy phase at ambient conditions. Here, the temperature at which the reservoir components are heated is just above the actual melting temperature of the pure drug contained in the formulation, producing a multi-phase drug-polymer system wherein at least one of the phases is enriched in drug. As with the former method, heating is continued in this method until all of the drug is observed to have melted.

This latter method, sometimes termed herein "Method B," will be particularly useful with drug-polymer systems wherein the selected drug has relatively low solubility in the polymeric material, typically less than about 10 wt. %, preferably less than about 5 wt. %, at the drug's melting temperature. This method will be particularly useful with silicone adhesives and polyisobutylenes. However, as above, each individual drug-polymer formulation will need to be evaluated independently to determine whether this method or the former method should be used.

Suitable polymeric materials for the drug reservoir are pressure-sensitive adhesives which are physically and chemically compatible with the drug to be administered, and the carriers and vehicles employed. Such adhesives include, for example, polysiloxanes, polyisobutylenes, polyacrylates, polyurethanes, plasticized ethylene-vinyl acetate copolymers, low molecular weight polyether amide block polymers (e.g., PEBAX), tacky rubbers such as polyisobutene, polystyrene-isoprene copolymers, polystyrene-butadiene copolymers, and mixtures thereof. Presently preferred adhesive materials for use as reservoir layer are acrylates, silicones and polyisobutylenes. Also preferred are the reservoir materials described in commonly assigned U.S. Pat. No. 5,252,334 to Chiang et al., i.e., combinations of acetate-acrylate copolymers (such as may be obtained under the trademarks GELVA® 737 and GELVA® 788 from Monsanto Chemical Co.) with a water soluble, water-absorptive polymer such as polyvinyl alcohol, gelatin, polyacrylic acid, sodium polyacrylate, methylcellulose, carboxymethylcellulose, polyvinylpyrrolidone, gum acacia, gum tragacanth, carrageenan and guar gum, particularly polyvinylpyrrolidone. As explained above, however, when Method A is used, acrylic adhesives and polyurethanes are preferred materials for the reservoir; when Method B is used, as noted above, preferred adhesives are generally silicones and polyisobutylenes.

Alternatively, pressure-sensitive, hot melt adhesives can be used, typically employing a melt coating or extrusion process. Examples of such hot melt, pressure-sensitive adhesives are adhesives based on styrene block copolymers, acrylics, polyisobutylenes.

Any number of drugs can be incorporated into transdermal delivery systems using the present methodology, so long as they are suitable for transdermal or transmucosal administration and give rise to the desired effect. Preferred drugs, however, are those which are capable of phase separation into a low thermodynamic activity form such as a crystalline structure, i.e., are capable of forming crystalline structures that have a lower thermodynamic activity and a reduced driving force for delivering drug across a membrane. Particularly preferred drugs are compounds which exist as solids, particularly although not necessarily crystalline solids, at room temperature. Reference may be had to Goodman and Gilman, *The Pharmacologica Basis of Therapeutics*, for the determination of such drugs.

Drugs which may be incorporated into transdermal systems using the present technique include, but are not limited to: analgesic serotonergic agonists; narcotic agonists and antagonists; anthistamines; antiinflammatory agents including NSAIDS (nonsteroidal antiinflammatory agents), benzodiazepines, dopaminergic agonists and antagonists; hormones, particularly steroids, and hormone antagonists; and antipsychotic agents.

Steroids represent one class of drugs which may be used in the present manufacturing technique. Examples of steroid drugs useful herein include: progestogens such as flurogestone acetate, hydroxyprogesterone, hydroxyprogesterone acetate, hydroxyprogesterone caproate, medroxyprogesterone acetate, norethindrone, norethindrone acetate, norethisterone, norethynodrel, desogestrel, 3-keto desogestrel, gestadene and levonorgestrel; estrogens such as estradiol and its esters (e.g., estradiol benzoate, valerate, cyprionate, decanoate and acetate), ethynyl estradiol, estriol, estrone and mestranol; corticosteroids such as betamethasone, betamethasone acetate, cortisone, hydrocortisone, hydrocortisone acetate, corticosterone, fluocinolone acetonide, prednisolone, prednisone and triamcinolone; and androgens and anabolic agents such as aldosterone, androsterone, testosterone and methyl testosterone.

The drug formulation may include, in addition to drug, a solvent effective to facilitate dissolution of the drug. When Method A is used, it is preferred to use a solvent in which the drug have high solubility. The choice of solvent will thus depend on the drug, but, generally, ethyl acetate, toluene, and alcohols such as methanol, ethanol and isopropanol will be suitable. With Method B, the choice of solvent is somewhat less important; virtually any solvent can be used so long as it is relatively easy to remove and favors processability of the drug-polymer admixture. If a solvent is used, it is removed during or before heat treatment. The temperature at which the solvent is removed, and the time required for solvent removal will depend, clearly, on the volatility of the solvent used. Solvent removal may be effected in a single step, or a two-step process, in which different times and temperatures are involved in each step, may be used.

The drug formulation may also include standard carriers or vehicles useful for facilitating drug delivery, e.g., stabilizers, antioxidants, anti-irritants, crystallization inhibitors (such as polyvinylpyrrolidone, cellulosic polymers, polyethylene oxide, polyvinyl alcohol, polyacrylic acid, gelatins, cyclodextrins, silica and the like). Cross-linking agents may also be included which will incorporate into the polymeric matrix.

Skin permeation enhancers may also be present in the drug formulation, although, as explained above, the present manufacturing technique reduces the need for enhancers by virtue of increasing the rate of drug release. If enhancers are incorporated in the device, they will generally represent on the order of approximately 1 wt. % to 25 wt. % of the drug formulation. Suitable enhancers include, but are not limited to, dimethylsulfoxide (DMSO), dimethyl formamide (DMF), N,N-dimethylacetamide (DMA), decylmethylsulfoxide ($C_{10}$MSO), polyethylene glycol monolaurate (PEGML), propylene glycol (PG), propylene glycol monolaurate (PGML), glycerol monolaurate (GML), methyl laurate (ML), lauryl lactate (LL), isopropyl myristate (IPM), terpenes such as menthone, $C_2$–$C_6$ diols, particularly 1,2-butanediol, lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. Vegetable oil permeation enhancers, as described in commonly assigned U.S. Pat. No. 5,229,130 to Sharma, may also be used. Such oils include, for example, safflower oil, cotton seed oil and corn oil.

Preferred drug formulations, i.e., the drug-containing composition which is loaded into the drug reservoir, will typically contain on the order of about 0.1 wt. % to 20 wt. %, preferably about 1 wt. % to 10 wt. % drug, with the remainder of the formulation representing other components such as enhancers, vehicles or the like.

One type of transdermal system which may be manufactured using the present technique is shown in FIG. 1. The composite, generally designated 10, comprises a backing layer 11, a reservoir layer 12 supersaturated with drug 12a, and a release liner 13. Such a structure is generally termed a "monolithic" transdermal system because the reservoir layer doubles as the adhesive which affixes the device to the skin.

The backing layer 11 functions as the primary structural element of the device and provides the device with much of its flexibility, drape and, preferably, occlusivity. The material used for the backing layer should be inert and incapable of absorbing drug, enhancer or other components of the pharmaceutical composition contained within the device. The backing is preferably made of one or more sheets or films of a flexible elastomeric material that serves as a protective covering to prevent loss of drug and/or vehicle via transmission through the upper surface of the device, and will preferably impart a degree of occlusivity to the device, such that the area of the skin covered on application becomes hydrated. The material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. Examples of materials useful for the backing layer are polyesters, polyethylene, polypropylene, polyurethanes and polyether amides. The layer is preferably in the range of about 15 microns to about 250 microns in thickness, and may, if desired, be pigmented, metallized, or provided with a matte finish suitable for writing.

The reservoir layer 12 in FIG. 1 doubles as the means for containing drug and as an adhesive for securing the device to the skin during use. That is, as release liner 13 is removed prior to application of the device to the skin, reservoir layer 12 serves as the basal surface of the device which adheres to the skin. Reservoir layer 12 is comprised of an adhesive material as described above, and will generally range in thickness from about 10 to about 300 microns, preferably approximating 75 microns.

Release liner 13 is a disposable element which serves only to protect the device prior to application. Typically, the release liner is formed from a material impermeable to the drug, vehicle and adhesive, and which is easily stripped from the contact adhesive. Release liners are typically treated with silicone or fluorocarbons. Silicone-coated polyester is presently preferred.

Figure 2:
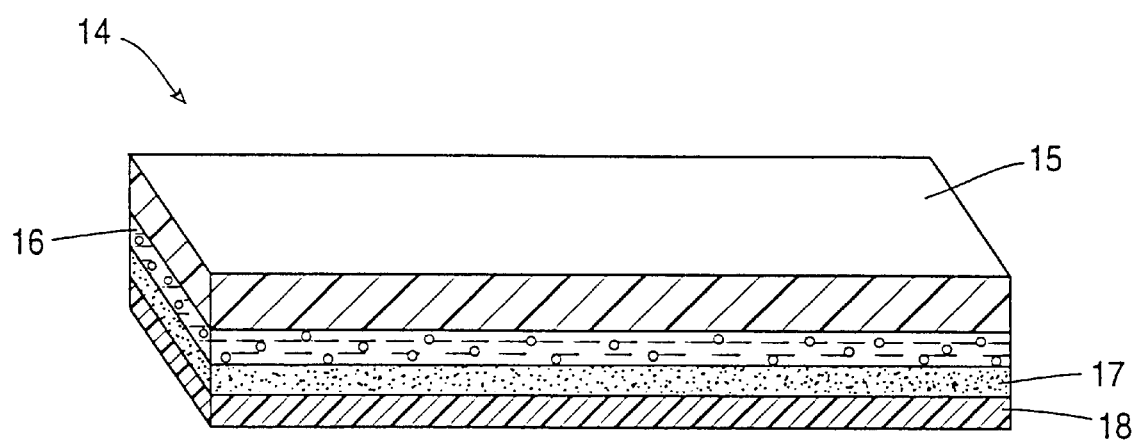
FIG. 2 illustrates in schematic form an alternative embodiment of a solid matrix-type transdermal delivery system which may be manufactured so as to contain a supersaturated drug reservoir as provided herein.

FIG. 2 illustrates a different type of laminated composite that may serve as the transdermal delivery system herein. That system is shown generally at 14, with backing layer 15, drug reservoir 16, contact adhesive layer 17, and release liner 18. The backing layer and release liner are as described above with respect to the structure of FIG. 1. With regard to drug reservoir 16 and contact adhesive layer 17, suitable materials are as described above, e.g., polysiloxanes, polyisobutylenes, polyacrylates, polyurethanes, plasticized ethylene-vinyl acetate copolymers, low molecular weight polyether amide block polymers, tacky rubbers, and mixtures thereof. An alternative to this type of structure, not shown, is where contact adhesive layer 17 is replaced with a peripheral ring of contact adhesive material which, again, serves to affix the transdermal device to the skin during drug delivery.

Any of the transdermal drug delivery devices manufactured using the present technique may also be provided with a release rate controlling membrane to assist in controlling the flux of drug and/or vehicle from the device. Such a membrane will be present in a drug delivery device beneath and typically immediately adjacent to the drug reservoir, and generally between the drug reservoir itself and an adhesive layer which affixes the device to the skin. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, and the like. A particularly preferred material useful to form the rate controlling membrane is ethylene-vinyl acetate copolymer.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

In the following examples, efforts have been made to ensure accuracy with respect to numbers used (e.g., amounts, temperature, etc.) but some experimental error and deviation should be accounted for. Unless indicated otherwise, temperature is in degrees C and pressure is at or near atmospheric.

EXPERIMENTAL

Materials and Methods

Micronized estradiol hemihydrate, USP grade, was obtained from Diosynth. DURO-TAK® 87-2287 is an acrylic pressure sensitive adhesive that is manufactured by National Starch and Chemical Company and contains 50 wt. % ethyl acetate which is removed during sample preparation. Silicone 4201 adhesive is manufactured by Dow Corning and contains 35 wt. % heptane. The PIB blend contains a ratio of 1:5:4 of HMW PIB (Exxon Vistanex® MML-100, M.W. 1,060,000–1,440,000) : LMW PIB (Exxon Vistanex® LM-MS-LC, M.W. 42,600–46,100) : polybutene (Amoco Indopol® H-1900, M.W. 2300) and is prepared in a solution with 60% hexane. Scotchpak® 1022 (3M) and 3-EST-A 242M (Release International) films were used as release liners when the adhesive is contacting the release side and backing materials when the adhesive is contacting the non-release side. The membrane used in the flux studies was Dow Corning Silastic® non-reinforced medical grade silicone rubber, 0.010" NRV (nominally 10 mil thick).

All flux experiments were run in triplicate, and the values reported represent the mean and standard deviation for three cells.

In Vitro Skin Permeation:

Skin Preparation: Human cadaver skin was used for the permeation studies. The frozen skins were thawed and the epidermal layers (stratum corneum and viable epidermis) were separated from the full-thickness skin by immersing it in water at 60° C. for two min. This epidermis was either used immediately for flux studies or stored at −20° C. for later studies.

Skin permeation from vehicles: Modified Franz diffusion cells were used for evaluating the performance of vehicles for drug delivery. The receiver compartment was filled with 7.5 ml of pH 7 buffer. Two hundred $\mu$l of the selected vehicles saturated with drug were then placed into the donor compartment to initiate the skin flux experiments. The temperature of the diffusion cell contents was maintained at 32° C.±1° C. At predetermined times, one ml of receiver content was withdrawn and replaced with fresh buffer. Samples were assays by HPLC.

Skin permeation from prototypes: Modified Franz cells were used for evaluating the prototype systems for drug delivery. The prototype systems were peeled off the polyester release liner and placed on top of the epidermis with the drug adhesive layer facing the stratum corneum. Gentle pressure was applied to insure full contact between the drug adhesive layer and the stratum corneum. The skin membrane with the prototype system was then mounted carefully between the donor and the receiver compartments. The receiver compartment was filled with pH 7 buffer and the temperature was maintained at 32° C.±1° C. throughout the experimental period. One ml of receiver content was withdrawn and replaced with fresh buffer. Samples were assayed by HPLC.

Flux determination: Skin flux ($\mu g/cm^2/hr$) was determined from the steady-state slope of the plot of the cumulative amount of drug permeated through the skin versus time. After steady state had been established, the linear portion of the plot was used to calculate the flux from the slope. Each formulation was run in triplicate, and the values reported represent the mean and standard deviation for three cells.

EXAMPLE 1

Laminates with 5, 10, 20, 40, and 80 wt. % estradiol (based on estradiol and adhesive solids) were prepared as follows. Appropriate amounts of micronized estradiol hemihydrate were added to DURO-TAK® 87-2287 containing ethyl acetate in order to prepare the desired concentrations of estradiol in adhesive solids. Additional ethyl acetate (up to twice the amount of estradiol hemihydrate) was added to the higher concentration samples in order to reduce the wet sample viscosity to aid mixing. The samples were mixed on a rotator overnight. In all cases, the resultant mixture contained a dispersion of crystalline estradiol in wet adhesive. Laminates were drawn down on the release side of 1022 film with a knife at 15 mil wet. The solvent was removed by drying in an oven at 70° C. for 1.5 hours. A second layer of 1022 film was laminated onto the adhesive, release side contacting adhesive, for storage of the laminates. Drug/adhesive samples (19–22 mg) were cut from the laminates with a blade, removed from both release liner films and transferred to large volume stainless steel capsules (Perkin Elmer) for Differential Scanning Calorimeter measurements.

Figure 3:
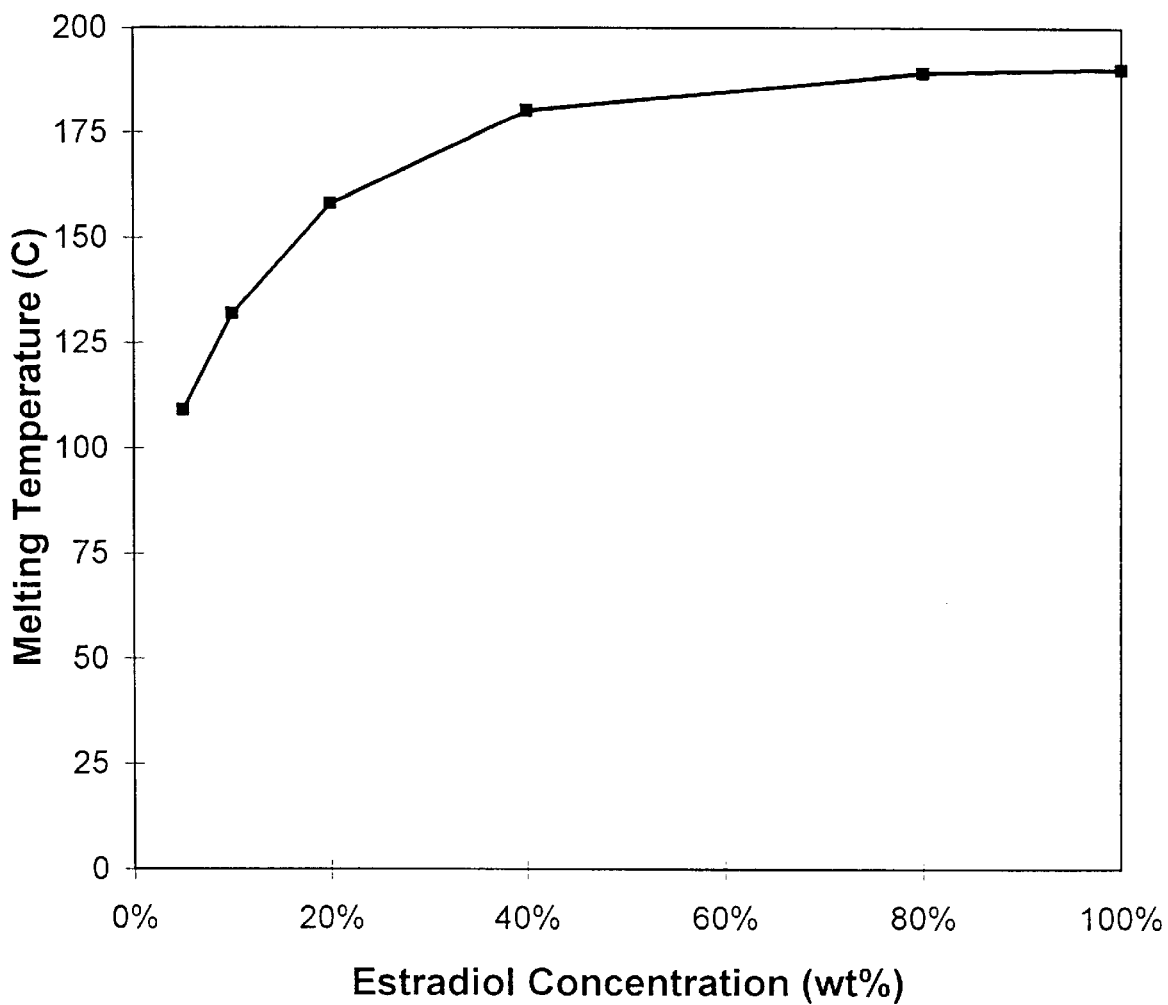
FIG. 3 is a phase diagram constructed by evaluating melting temperature as a function of estradiol concentration, in the system of Example 1.

The phase diagram of estradiol in DURO-TAK® 87-2287 was determined by measuring melting endotherms during a heating scan on a differential scanning calorimeter (Perkin Elmer DSC 7). Heating scans were performed with a rate of 10° C./min. A phase diagram was constructing by evaluated melting temperature as a function of estradiol concentration (see Table 1) and is shown in FIG. 3. Samples of 40 wt. % estradiol and less have melting temperatures that are significantly less than that for pure estradiol. When these samples are heated to a temperature above their melting temperature, the samples become a single phase of drug dissolved in adhesive as is evidenced by their transparent appearance. The 80 wt. % sample exhibited a melting temperature that is identical to that for the pure drug, within experimental error. A sample such as this is turbid after heating above the melting temperature, indicating a high concentration estradiol liquid phase has separated from the polymer phase.

TABLE 1

Melting Temperatures for
Estradiol in DURO-TAK ® 2287

| Concentration of Estradiol (wt. %) | Melting Temperature (° C.) |
|---|---|
| 5 | 109 |
| 10 | 132 |
| 20 | 158 |
| 40 | 180 |
| 80 | 189 |
| 100 | 190 |

EXAMPLE 2

Laminates with 5 wt. % estradiol in DURO-TAK® 87-2287 were prepared similar to the procedure in Example 1, coating onto the release side of 3-EST-A 242M film. Solvent was removed by drying in an oven at 70° C. for one hour. The non-release side of a second piece of 3-EST-A 242M film was laminated to the adhesive to serve as a backing material. A portion of a 5 wt. % laminate was subjected to a heat treatment at 140° C.±10° C. for one hour. Note that this temperature is greater than the melting temperature for the 5 wt. % sample in Example 1 and is substantially less than the melting temperature of the pure drug.

Figure 4:
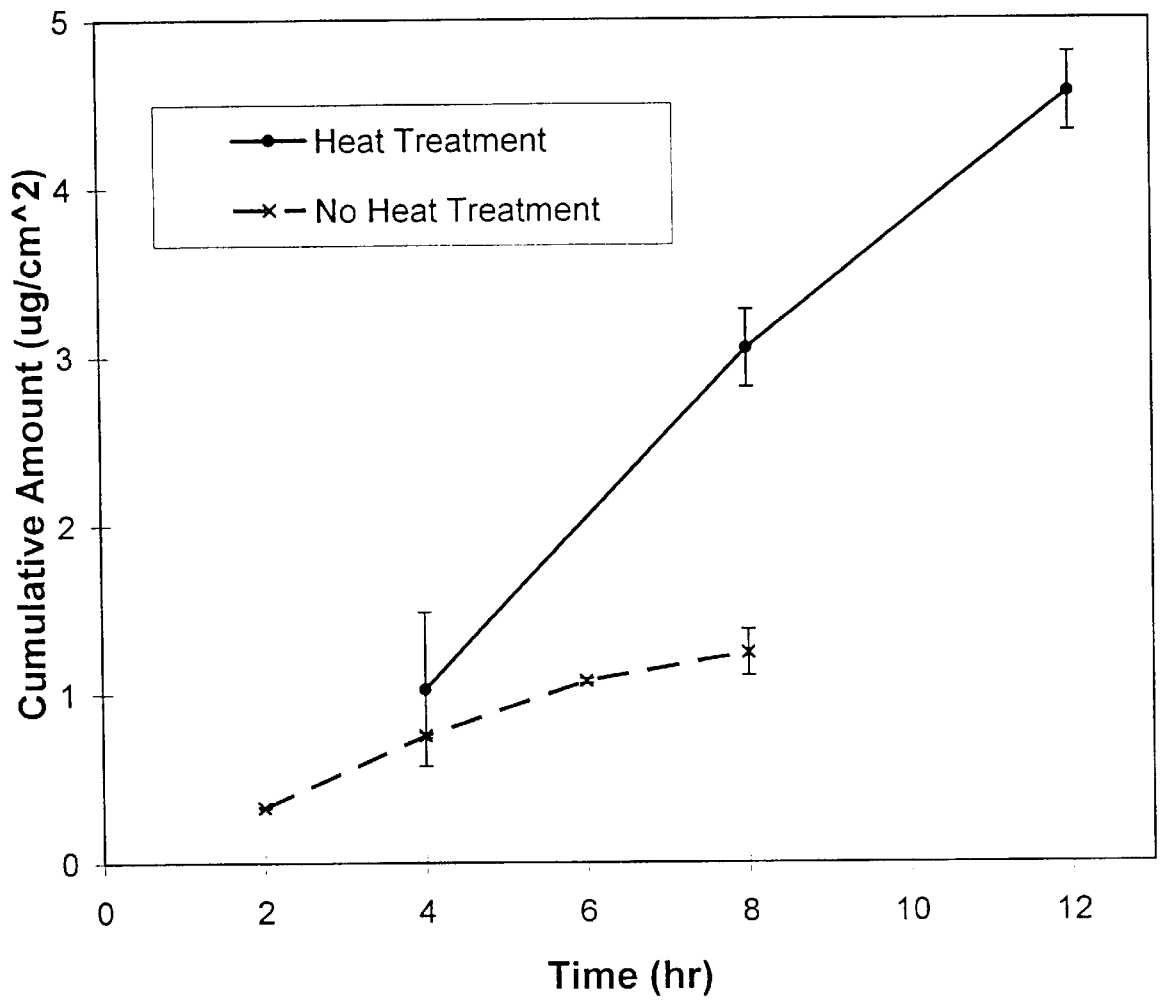
FIGS. 4, 5, 6 and 7 are graphs showing the cumulative amount of estradiol delivered from the heat-treated and non heat-treated systems evaluated in Examples 2, 3, 4 and 5, respectively.

Disks of the laminates were punched out with a die (3/8" for the heat-treated sample, 5/8" for the nonheat-treated samples). In addition, 5/8" disks of Silastic® membrane were also punched with a die. The release liner was removed from the sample and the sample was laminated to the Silastic® membrane. The composite was mounted on a diffusion cell with the receiver solution (0.9% NaCl and 0.01% $NaN_3$) contacting the Silastic® membrane side of the composite. At appropriate sampling time points, the entire receiver solution was removed and replaced by fresh solution. The concentration of estradiol in the receiver solution was measured with a standard HPLC method. The cumulative amount of estradiol delivered across Silastic® membrane is displayed in FIG. 4. The heat-treated 5 wt. % sample delivered twice as much estradiol after eight hours compared to the 5 wt. % sample that was not heat treated.

EXAMPLE 3

A portion of the 20 wt. % estradiol in DURO-TAK® 87-2287 from Example 1 was used in the following flux study. One of the 1022 films that had been laminated with the release side contacting the adhesive was removed. Another piece of 1022 film was laminated to the adhesive via the non release side in order to serve as a backing material. A portion of this laminate was heat treated in an oven at 185° C.±10° C. for 30 minutes and subsequently quenched to room temperature by removing it from the oven. As may be concluded from Table 1, this sample exhibited a depressed melting temperature and, hence, was a single-phase solution after heat treatment.

Figure 5:
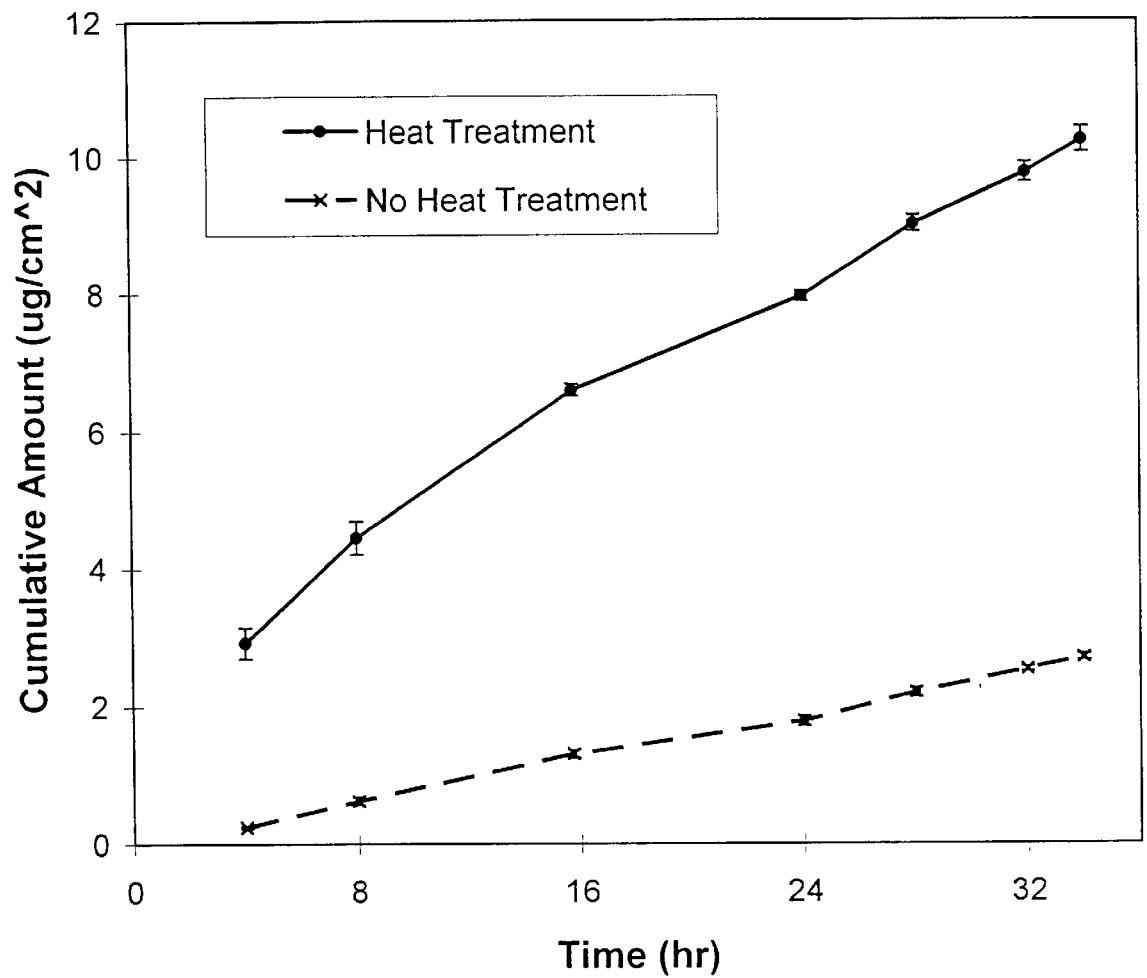

Disks of the heat-treated and nonheat-treated laminates (3/8") were punched out with a die. In addition, 5/8" disks of Silastics membrane were also punched with a die. The samples were laminated to Silastic® membrane and flux experiments were performed using the same procedure as in Example 2. A comparison of the cumulative amount of estradiol delivered through a Silastic® membrane is displayed in FIG. 5. Heat treatment, in this case, was found to increase the amount of estradiol delivered across the Silastic® membrane by a factor of four.

EXAMPLE 4

Figure 6:
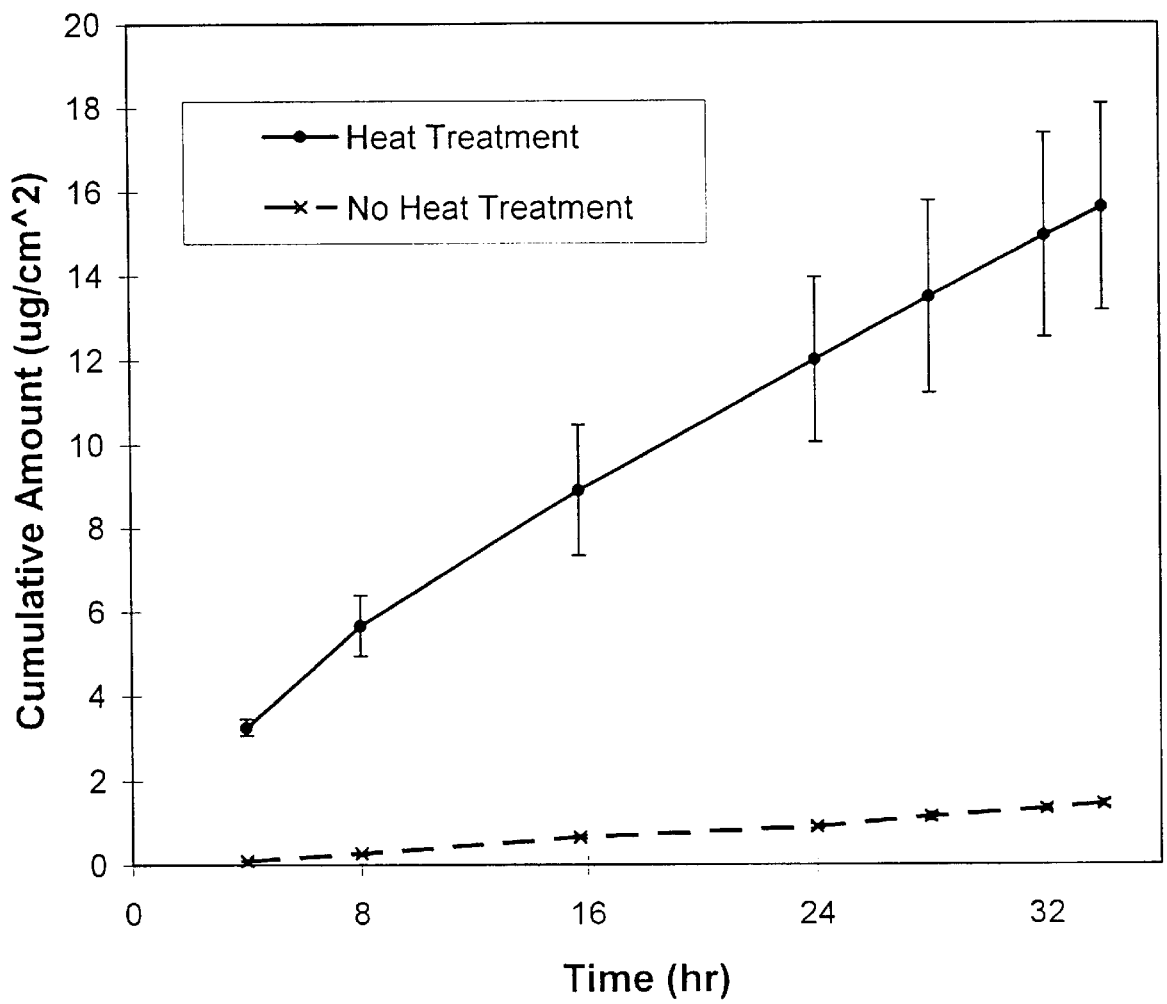

A sufficient amount of micronized estradiol hemihydrate was added to Silicone 4201 containing heptane in order to prepare a laminate with 20 wt. % estradiol in adhesive solids. The samples were mixed on a rotator overnight. The resultant mixture contained a dispersion of crystalline estradiol in wet adhesive. A laminate was drawn down on the release side of 1022 film with a knife at 15 mil wet. The solvent was removed by drying in an oven at 70° C. for 1 hour. A portion of this laminate was heat treated in an oven at 185° C.±10° C. for 30 minutes and subsequently quenched to room temperature by removing it from the oven. Since the estradiol concentration in this sample is well above the solubility of the drug in Silicone 4201 at the drug melting temperature (0.8 wt. %, as determined by DSC), this sample was multi-phase following heat treatment. The heat-treated and nonheat-treated samples were run in the flux study described in Example 3. The results are displayed in FIG. 6, and reveal an order of magnitude increase in the amount of estradiol delivered across the Silastic® membrane.

EXAMPLE 5

Figure 7:
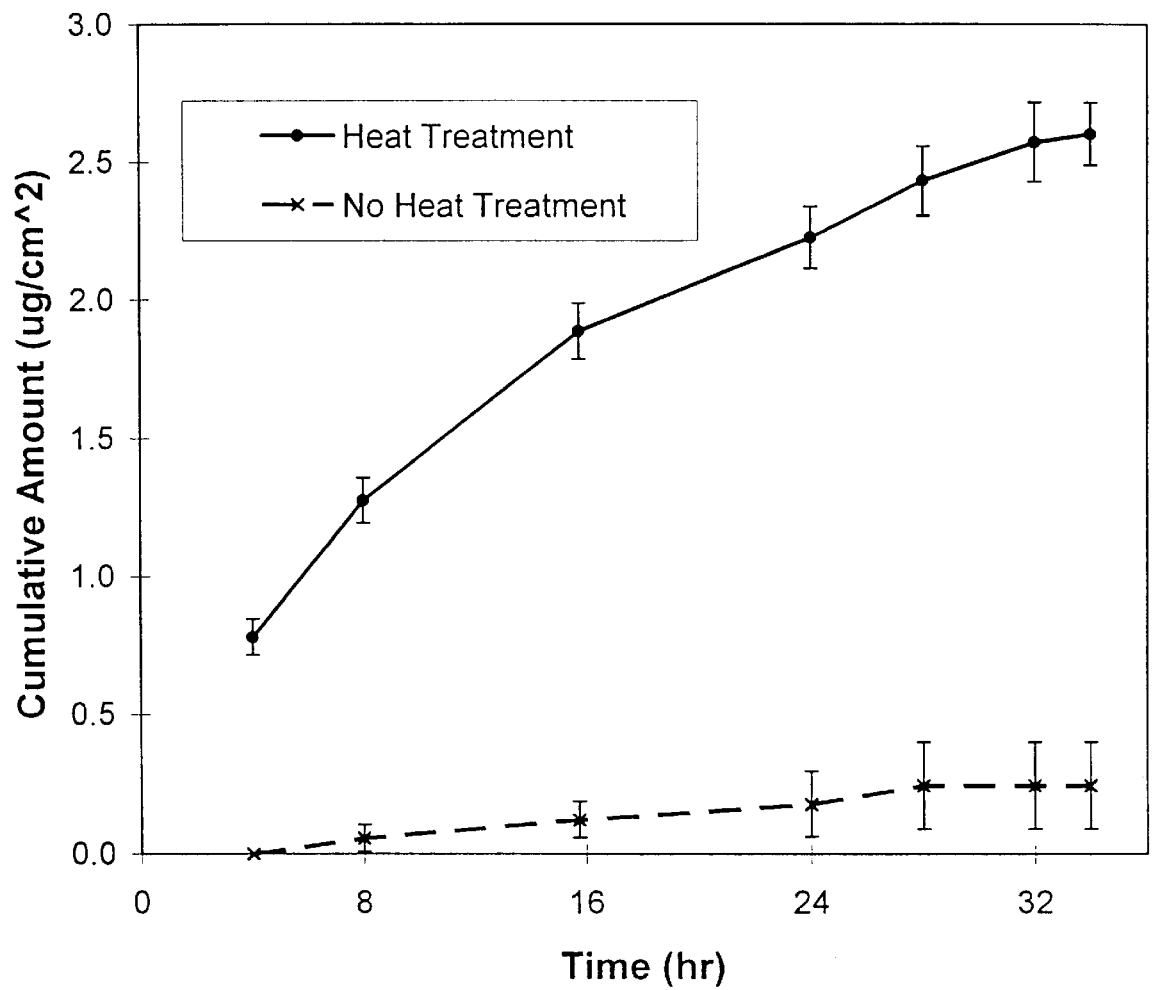

A sample of 20 wt. % estradiol in a PIB blend (see materials section, above, for further information) was prepared using a method identical to that described in Example 4, including the heat treatment of a portion of the sample. As in Example 4, the estradiol concentration in the sample was well above the solubility of the drug in PIB at the drug melting temperature (3 wt. %, determined by DSC). This sample was multi-phase following heat treatment. Again, the heat-treated and nonheat-treated samples were run in the flux study described in Example 3. The results displayed in FIG. 7 illustrate that over an order of magnitude increase in estradiol delivery is obtained when this sample is subjected to the heat treatment method of the invention.

We claim:

1. A method for preparing a supersaturated drug reservoir for incorporation into a transdermal drug delivery device, comprising:

(a) admixing a polymeric material and a drug formulation compatible therewith to form a drug-polymer admixture;

(b) removing substantially all solvent if present in the drug-polymer admixture;

(c) evaluating the depressed melting temperature of the drug-polymer admixture of step (b);

(d) heating the admixture prepared in step (b) to a predetermined temperature, effective to dissolve the drug in the polymeric material, wherein the predetermined temperature is above the depressed melting temperature determined in step (c); and (e) cooling the heated admixture of step (d) to form a drug reservoir, wherein the relative quantities of drug and polymeric material are such that the drug reservoir contains on the order of 0.1 wt. % to 20 wt. % drug.

2. The method of claim 1, wherein the drug formulation contains a solvent effective to dissolve the drug.

3. The method of claim 2, wherein the polymeric material comprises a pharmaceutically acceptable pressure-sensitive adhesive.

4. The method of claim 1, wherein the drug is selected on the basis of its capability to phase separate into a low thermodynamic activity form.

5. The method of claim 4, wherein the low thermodynamic activity form is a crystalline structure.

6. The method of claim 4, wherein the drug exists as a solid at room temperature.

7. The method of claim 4, wherein the drug is a steroid.

8. The method of claim 7, wherein the drug is selected from the group consisting of progestogens, estrogens, corticosteroids and androgens.

9. The method of claim 8, wherein the drug is selected from the group consisting of flurogestone acetate, hydroxyprogesterone, hydroxyprogesterone acetate, hydroxyprogesterone caproate, medroxyprogesterone acetate, norethindrone, norethindrone acetate, norethisterone, norethynodrel, desogestrel, 3-keto desogestrel, gestadene, levonorgestrel, estradiol, estradiol benzoate, estradiol valerate, estradiol cyprionate, estradiol decanoate, estradiol acetate, ethynyl estradiol, estriol, estrone, mestranol, betamethasone, betamethasone acetate, cortisone, hydrocortisone, hydrocortisone acetate, corticosterone, fluocinolone acetonide, prednisolone, prednisone, triamcinolone, aldosterone, androsterone, testosterone and methyl testosterone.

10. The method of claim 9, wherein the drug is estradiol.

11. A supersaturated drug reservoir prepared by the process of claim 1.

12. A method for preparing a supersaturated drug reservoir for incorporation into a transdermal drug delivery device, comprising:

(a) admixing a polymeric material and a drug formulation to form a drug-polymer admixture;

(b) determining the depressed melting temperature of the drug-polymer admixture wherein the drug-polymer admixture is substantially solvent-free;

(c) heating the admixture prepared in step (a) to a predetermined temperature effective to dissolved the drug in the polymeric mixture, wherein the predetermined temperature is above the depressed melting temperature determined in step (b); and (d) cooling the heated admixture of step (c) to form a drug reservoir.

13. The method of claim 12, wherein any solvent present in the drug-polymer admixture is substantially removed during step (c).

14. The method of claim 12, wherein any solvent present in the drug-polymer admixture is substantially removed prior to step (c).

* * * * *